US012653817B2

(12) United States Patent
Lu et al.

(10) Patent No.: US 12,653,817 B2
(45) Date of Patent: Jun. 16, 2026

(54) PHARMACEUTICAL COMPOSITION COMPRISING PROTEIN KINASE INHIBITOR AND CHEMOTHERAPEUTIC DRUG AND USE THEREOF

(71) Applicants: SHENZHEN CHIPSCREEN BIOSCIENCES CO., LTD., Shenzhen (CN); CHENGDU CHIPSCREEN PHARMACEUTICAL CO., LTD, Sichuan (CN)

(72) Inventors: Xianping Lu, Shenzhen (CN); Zhiqiang Ning, Shenzhen (CN); Xiaoning Wang, Shenzhen (CN)

(73) Assignees: SHENZHEN CHIPSCREEN BIOSCIENCES CO., LTD., Shenzhen (CN); CHENGDU CHIPSCREEN PHARMACEUTICAL CO., LTD, Sichuan (CN)

( * ) Notice: Subject to any disclaimer, the term of this patent is extended or adjusted under 35 U.S.C. 154(b) by 804 days.

(21) Appl. No.: 17/914,324

(22) PCT Filed: Mar. 24, 2021

(86) PCT No.: PCT/CN2021/082656
§ 371 (c)(1),
(2) Date: Sep. 24, 2022

(87) PCT Pub. No.: WO2021/190546
PCT Pub. Date: Sep. 30, 2021

(65) Prior Publication Data

US 2023/0117545 A1 Apr. 20, 2023

(30) Foreign Application Priority Data

Mar. 24, 2020 (CN) ........................ 202010212751.5

(51) Int. Cl.

| | |
|---|---|
| ***A61K 31/47*** | (2006.01) |
| ***A61K 9/48*** | (2006.01) |
| ***A61K 31/337*** | (2006.01) |
| ***A61K 31/7048*** | (2006.01) |
| ***A61P 15/08*** | (2006.01) |
| ***A61P 35/00*** | (2006.01) |

(52) U.S. Cl.
CPC ................ *A61K 31/47* (2013.01); *A61K 9/48* (2013.01); *A61K 31/337* (2013.01); *A61K 31/7048* (2013.01); *A61P 15/08* (2018.01); *A61P 35/00* (2018.01)

(58) Field of Classification Search
CPC ........ A61K 31/47; A61K 9/48; A61K 31/337; A61K 31/7048; A61P 15/08; A61P 35/00
See application file for complete search history.

(56) References Cited

FOREIGN PATENT DOCUMENTS

| | | | | |
|---|---|---|---|---|
| CN | 101906076 A | | 12/2010 | |
| EP | 2439195 A1 | | 4/2012 | |
| EP | 2439195 B1 | * | 7/2014 | ............. A61P 11/00 |
| WO | 2020/034916 A1 | | 2/2020 | |

OTHER PUBLICATIONS

Maoz A, Ciccone MA, Matsuzaki S, Coleman RL, Matsuo K. Emerging serine-threonine kinase inhibitors for treating ovarian cancer. Expert Opin Emerg Drugs. Dec. 2019;24(4):239-253. (Year: 2019).*
Andrew R. Reynolds et al., Cancer Discov (2023) 13 (5): 1058-1083. (Year: 2023).*
Sarah M. Temkin, Clin Obstet Gynecol. Dec. 2017; 60(4): 738-757. (Year: 2017).*
NCT03901118 (ClinicalTrials.gov, Jul. 22, 2019, Chiauranib in Combination With Chemotherapy in Patients With Ovarian Cancer. (Year: 2019).*
Sun, Y., Yang, L., Hao, X. et al. Phase I dose-escalation study of chiauranib, a novel angiogenic, mitotic, and chronic inflammation inhibitor, in patients with advanced solid tumors. J Hematol Oncol 12, 9 (2019). (Year: 2019) .*
International Search Report for PCT/CN2021/082656 mailed Jun. 28, 2021, ISA/CN.
Shenzhen Microchip Biotechnology Co., Ltd., Clinical Study of Cioronib in Combination with Chemotherapy for Platinum-Refractory/ Platinum-Resistant Recurrent Ovarian Cancer, http://www.cancer123.com/treatment/1070/, Apr. 5, 2019 (Apr. 5, 2019), pp. 1-11.
Maoz. Asaf et al., Emerging Serine-Threonine Kinase Inhibitors for Treating Ovarian Cancer, Expert Opinion on Emerging Drugs, vol. 24, No. 4. Dec. 31, 2019 (Dec. 31, 2019), pp. 239-253.
Chipscreen Biosciences Ltd., Phase Ib Study of Chiauranib in Patients With Ovarian Cancer, https://clinicaltrials.gov/ct2/show/NCT03166891, Jan. 18, 2020 (Jan. 18, 2020), pp. 1-8.
Sun, Yongkun et al., Phase I Dose-Escalation Study of Chiauranib, a Novel Angiogenic, Mitotic, and Chronic Inflammation Inhibitor, in Patients with Advanced Solid Tumors, Journal of Hematology & Oncology, Jan. 14, 2019 (Jan. 14, 2019), pp. 1-10.
M. Gaestel, et al., Protein Kinases as Small Molecule Inhibitor Targets in Inflammation, Current Medicinal Chemistry, (2007) 14:2214-2234.

(Continued)

*Primary Examiner* — Clinton A Brooks
*Assistant Examiner* — Izabela Schmidt
(74) *Attorney, Agent, or Firm* — Yue (Robert) Xu; Apex Attorneys at Law, LLP

(57) ABSTRACT

The present invention relates to the field of biotechnology, and in particular relates to a pharmaceutical composition comprising a protein kinase inhibitor and a chemotherapeutic drug and use thereof. It is found that in the treatment of platinum-refractory/drug-resistant relapsed advanced ovarian cancer, the remission rates of etoposide or paclitaxel in combination with chiauranib is respectively 40% and 50%, while the remission rate of etoposide alone is about 27%, and the remission rate of paclitaxel alone is about 21%, indicating that the combination of chiauranib and etoposide or paclitaxel in the treatment of platinum-refractory/drug-resistant relapsed advanced ovarian cancer has achieved unexpected synergistic effects.

6 Claims, No Drawings

(56) References Cited

OTHER PUBLICATIONS

Hanks and Hunter, The eukaryotic protein kinase superfamily: kinase (catalytic) domain structure and classification, (1995), FASEB J. 9: 576-596.
Daniel R. Knighton, et al., Crystal Structure of the Catalytic Subunit of Cyclic Adenosine Monophosphate-Dependent Protein Kinase, Science, (1991) 253: 407-414.
Ian D. Hiles, et al., Phosphatidylinositol 3-Kinase:Structure and Expression of the 110 kd Catalytic Subunit, Cell, (1992), 70:419-429.
Jeannette Kunz, et al., Target of Rapamycin in Yeast, TOR2, Is an Essential Phosphatidylinositol Kinase Homolog Required for G1 Progression, Cell (1993), 73:585-596.
Jose F. Garcia-Bustos, et al., PIK1, an essential phosphatidylinositol 4-kinase associated with the yeast nucleus, EMBO J., (1994), 13:2352-2361.
Michael C. Heinrich, et al., Inhibition of c-kit receptor tyrosine kinase activity by STI 571, a selective tyrosine kinase inhibitor, Blood 2000, 96(3):925-32.
Search Report dated Mar. 21, 2024 for European patent application No. 21774279.0.
You Zhou et al: "CS2164, a novelmulti-target inhibitor against tumor angiogenesis, mitosis and chronic inflammation with anti-tumor potency", Cancer Science, vol. 108, No. 3, Mar. 1, 2017 (Mar. 1, 2017) , pp. 469-477.
Anonymous: "Record History Iver. 3: 2019-07-22 I NCT03901118 I ClinicalTrials.gov", Jul. 22, 2019 (Jul. 22, 2019), XP093139507.

* cited by examiner

PHARMACEUTICAL COMPOSITION COMPRISING PROTEIN KINASE INHIBITOR AND CHEMOTHERAPEUTIC DRUG AND USE THEREOF

This application is the national phase of International Application No. PCT/CN2021/082656, titled "PHARMACEUTICAL COMPOSITION COMPRISING PROTEIN KINASE INHIBITOR AND CHEMOTHERAPEUTIC DRUG AND USE THEREOF", filed on Mar. 24, 2021, which claims the priority to Chinese Patent Application No. 202010212751.5, titled "PHARMACEUTICAL COMPOSITION COMPRISING PROTEIN KINASE INHIBITOR AND CHEMOTHERAPEUTIC DRUG AND USE THEREOF", filed on Mar. 24, 2020 with the China National Intellectual Property Administration, which is incorporated herein by reference in entirety.

FIELD

The present disclosure relates to the field of biotechnology, and in particular to a pharmaceutical composition comprising a protein kinase inhibitor and a chemotherapeutic drug and use thereof.

BACKGROUND

Protein B kinases are a family of enzymes that catalyze the phosphorylation of specific residues in proteins, broadly divided into tyrosine and serine/threonine kinases, which represent a large family of proteins that play important roles in regulating a variety of cellular processes and maintaining cellular functions. Protein kinases are enzymatic components of signal transduction pathways that catalyze the transfer of terminal phosphates of ATP to the hydroxyl groups of tyrosine, serine and/or threonine residues in proteins. Overexpression or inappropriate expression of normal or mutated protein kinases in mammals has been a subject of extensive research and it has been shown to play an important role in the development of many diseases, including cancer. A partial non-limiting list of these kinases comprises: non-receptor tyrosine kinases, such as the Janus kinase family (Jak1, Jak2, Jak3, and Tyk2); receptor tyrosine kinases, such as platelet-derived growth factor receptor kinase (PDGFR); and serine/threonine kinases such as b-RAF. Aberrant kinase activity is observed in a number of disease states, comprising benign and malignant proliferative disorders and diseases resulted from inappropriate activation of the immune and nervous systems.

Protein kinases, as a large family of structurally related enzymes, are responsible for the control of various signal transduction processes in cells (e.g., Hardie and Hanks, The Protein Kinase Facts Book, I and II, Academic Press, San Diego, Calif., 1995). Protein kinases are thought to have evolved from a common ancestral gene due to the conservation of their structure and catalytic function. Almost all kinases contain similar catalytic domains of 250-300 amino acids. Kinases can be classified into various families according to their phosphorylated receptors (such as protein-tyrosine, protein-serine/threonine, and lipids). Sequence motifs that generally correspond to each of these families have been identified (e.g., Hanks and Hunter, (1995), FASEB J. 9: 576-596; Knighton et al., Science, (1991) 253: 407-414; Hiles et al., Cell, (1992), 70:419-429; Kunz et al., Cell (1993), 73:585-596; Garcia-Bustos et al., EMBO J., (1994), 13:2352-2361).

Inappropriate kinase activity resulted from mutation, overexpression or inappropriate regulation, abnormal regulation or dysregulation, and overproduction or underproduction of growth factors or cytokines can be involved in many diseases including, but not limited to, cancer and other diseases. Protein kinases have emerged as an important class of enzymes that are targets for therapeutic intervention. In particular, overactivation of the tyrosine kinase cKit is associated with hematological malignancies, and the tyrosine kinase cKit is a target for cancer therapy (Heinrich, Griffith et al., Blood 2000, 96(3):925-32). Likewise, signal transduction of JAK3 has been implicated in leukemias and lymphomas, and JAK3 is currently used as a potential therapeutic target (Heinrich, Griffith et al., 2000). Protein kinases also play a central role in regulation of cell cycle. It has been found that defects in various components of signal transduction pathways can cause a variety of diseases, including various forms of cancer (Gaestel et al., Current Medicinal Chemistry, (2007) 14:2214-2234). In recent years, protein kinases involved in oncogenic signaling pathways have become important drug targets in the treatment of various diseases including various types of cancer. There are also a variety of protein kinase inhibitors used as antitumor drugs.

Chiauranib is a new protein kinase inhibitor with complete intellectual property rights, which was developed independently by Shenzhen Chipscreen Biosciences Co., Ltd. Chiauranib is a small molecule anti-tumor targeting drug that targets multiple protein kinases, and it has a three-way anti-tumor synergistic mechanism of anti-tumor angiogenesis, inhibition of tumor cell mitosis, and regulation of tumor inflammatory microenvironment through high selective inhibitory activity against VEGFR/PDGFR/c-Kit, Aurora B, and CSF-1R targets, exerting a comprehensive anti-tumor effect. Compared with traditional VEGFR targeted inhibitors (such as sunitinib, sorafenib), the inhibitory activity of Chiauranib on Aurora B, a key enzyme in mitosis, is unique, and this product has the potential to reduce genomic instability in tumor tissue and to inhibit tumor cell metastasis. Chiauranib exerts anti-tumor activity through three complementary mechanisms including inhibiting tumor angiogenesis, cell mitosis and tumor inflammatory microenvironment, and its high target selectivity also reduces the risk of side effects caused by off-target effects.

DNA topoisomerases are important intracellular ribozymes that change the topological structure of DNA mainly through catalysis. Topoisomerases in eukaryotic cells are mainly divided into topoisomerase I (Topo I) and topoisomerase II (Topo II). Among them, the intermediate product formed during the catalytic process that causes the transient DNA double-strand break is called Topo II. Topo II plays an important role in important cellular life processes such as DNA replication, transcription and mitosis.

The role of DNA Topo II is to mediate DNA double-strand unwinding (breaking and religation). Normally, DNA Topo II forms a breakable complex with DNA. Topo II inhibitors are a class of anti-tumor drugs that target Topo II, and their anti-cancer effect is not to inhibit the activity of the enzyme itself, but to promote the formation of the enzyme-DNA breakable complex, so that the equilibrium reaction tends to the enzyme-DNA breakable complex, so as to prolong the half-life of the complex and stabilize it, and interfere with the DNA religation mediated by DNA Topo II, resulting in DNA single-strand or double-strand breaks, affecting DNA replication, thereby exerting a cell killing effect. The formation and stable existence of the breakable complex promotes abnormal recombination of DNA, thereby initiating the apoptosis program and leading to death of cell.

Based on the understanding of the key role of Topo II in cells, the research on such compounds has always been one of the hot spots in the development of anti-tumor drugs. Currently marketed topoisomerase II comprises etoposide, teniposide, etc.

Paclitaxel is the best natural anticancer drug that has been discovered, which has been clinically widely used in the treatment of breast cancer, ovarian cancer and some head and neck cancers and lung cancers. As a diterpene alkaloid compound with anticancer activity, paclitaxel has been favored by botanists, chemists, pharmacologists and molecular biologists due to its novel and complex chemical structure, extensive and significant biological activity, new and unique mechanism of action, and great shortage of natural resources, making it a worldwide anti-cancer star and research focus in the second half of the 20th century. Paclitaxel derivatives such as docetaxel and nab-paclitaxel have similar efficacy to paclitaxel.

In China, the annual incidence of ovarian cancer ranks third among female reproductive system tumors, after cervical cancer and uterine corpus malignant tumors, showing an elevating trend year by year, and the mortality rate of ovarian cancer ranks first among female reproductive tract malignant tumors, for which ovarian cancer is a malignant tumor seriously threatening women health. Ovarian malignant tumors comprise a variety of pathological types, the most common one of which is epithelial carcinoma, accounting for about 70% of ovarian malignant tumors, followed by malignant germ cell tumors and sex cord stromal tumors, accounting for about 20% and 5% respectively.

The treatment of ovarian cancer has always been the most difficult challenge faced by gynecological tumors, wherein the ideal cytoreductive surgery is the cornerstone of the treatment. Platinum-based combined chemotherapy regimen is the main chemotherapy regimen for ovarian cancer. However, even if the patients with advanced stage achieve complete response after the above treatment, 70% to 80% of them are still relapsed.

Platinum-refractory/platinum-resistant relapsed advanced ovarian cancer is the most difficult problem in clinical treatment, therefore it is of great significance to provide new treatment ideas for platinum-refractory/platinum-resistant relapsed advanced ovarian cancer, and explore to find an effective treatment for platinum-refractory/platinum-resistant advanced ovarian cancer.

SUMMARY

In the present disclosure, it is found that a pharmaceutical composition comprising a protein kinase inhibitor and a chemotherapeutic drug has an unexpected therapeutic effect on cancer, especially platinum-refractory/platinum-resistant relapsed advanced ovarian cancer.

In a first aspect, the present disclosure provides a pharmaceutical composition comprising a protein kinase inhibitor and a chemotherapeutic drug, wherein the protein kinase inhibitor comprises the compound described in CN200910223861.5, the entire content of which is incorporated herein by reference, and the protein kinase inhibitor is preferably a compound of formula (I):

(I)

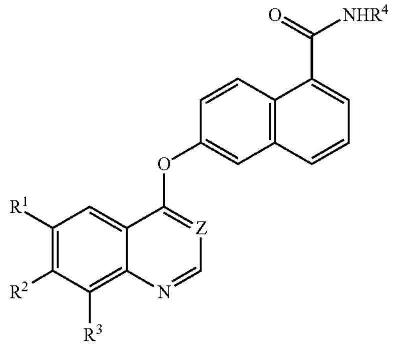

or its free form, salt form, enantiomer or diastereomer thereof, wherein Z is CH or N;

$R^1$, $R^2$ and $R^3$ are respectively hydrogen, halogen, methyl, methoxy or trifluoromethyl;

$R^4$ is

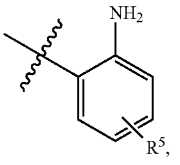

or

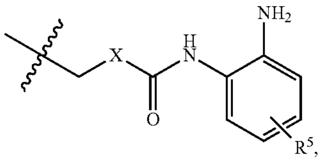

X is a benzene ring or a pyridine ring;

$R^5$ is one or more substituents selected from the group consisting of hydrogen, halogen, methyl, methoxy or trifluoromethyl.

In a preferred embodiment, the protein kinase inhibitor is a compound of formula (II), whose chemical name is N-(2-aminophenyl)-6-(7-methoxyquinoline-4-oxy)-1-naphthamide, commonly known as chiauranib:

(II)

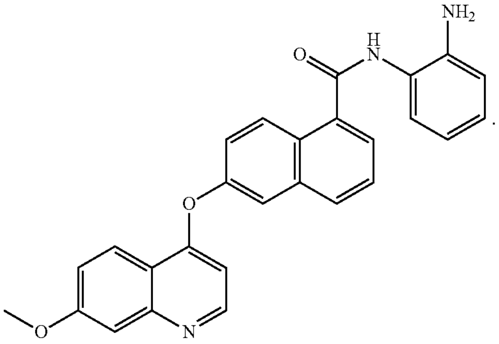

The chemotherapeutic drug comprises topoisomerase II inhibitors or paclitaxel and derivatives thereof; wherein, the topoisomerase II inhibitors comprise etoposide or teniposide; the paclitaxel and derivatives thereof comprise paclitaxel, docetaxel and nab-paclitaxel.

The protein kinase inhibitor is used at an amount within the range of 1-100 mg, preferably 20-80 mg, most preferably 50 mg. The topoisomerase II inhibitor is used at an amount within the range of 1-100 mg, preferably 20-80 mg, most preferably 50 mg. The paclitaxel and derivatives thereof are used at an amount within the range of 10-200 mg/$m^2$, preferably 50-100 mg/$m^2$, and most preferably 60 mg/$m^2$.

The pharmaceutical composition may also comprise a pharmaceutically acceptable carrier.

In a second aspect, the present disclosure provides use of the above pharmaceutical composition in the preparation of a medicament for preventing and/or treating cancer, wherein the cancer is ovarian cancer, and the ovarian cancer comprises malignant epithelial ovarian cancer, fallopian tube cancer and primary peritoneal carcinoma.

In a preferred embodiment, the cancer is platinum-refractory/platinum-resistant relapsed ovarian cancer, the platinum-refractory refers to tumor progression during treatment with a platinum-containing regimen, and the platinum-resistant refers to tumor progression or relapse within 6 months after the end of treatment with platinum-containing treatment regimen.

In a preferred embodiment, the cancer is platinum-refractory/platinum-resistant relapsed advanced ovarian cancer, wherein the advanced stage comprises stage III and stage IV. Stage III: tumor involving one or both ovaries or fallopian tubes, or primary peritoneal carcinoma, with cytologically or histologically confirmed peritoneal spread outside the pelvis, and/or metastasis to retroperitoneal lymph nodes. Stage IV: distant metastasis outside the abdominal cavity.

In a third aspect, the present disclosure provides a method for treating and/or preventing cancer, comprising the step of administering a therapeutically effective amount of the above-mentioned pharmaceutical composition to a patient in need, wherein the cancer is ovarian cancer, preferably platinum-refractory/platinum-resistant relapsed ovarian cancer, most preferably platinum-refractory/platinum-resistant relapsed advanced ovarian cancer.

In a preferred embodiment, the protein kinase inhibitor of the pharmaceutical composition is used at an amount of 1-100 mg, preferably 20-80 mg, most preferably 50 mg; and the protein kinase inhibitor is preferably an oral dosage form, most preferably a capsule, which is preferably taken orally every morning on an empty stomach, once a day.

In a preferred embodiment, the topoisomerase II inhibitor of the pharmaceutical composition is used at an amount of 1-100 mg, preferably 20-80 mg, most preferably 50 mg; and the topoisomerase II inhibitor is preferably an oral dosage form, most preferably a capsule, which is preferably taken orally every morning on an empty stomach, continuously administered for 21 days and suspended for 7 days, and every 28 days is a treatment cycle, with a maximum of 6 treatment cycles.

In a preferred embodiment, the paclitaxel and derivatives thereof of the pharmaceutical composition are used at an amount of 10-200 mg/$m^2$, preferably 50-100 mg/$m^2$, most preferably 60 mg/$m^2$; and the paclitaxel and derivatives thereof are preferably a parenteral administration dosage form, more preferably an intravenous administration dosage form, which are preferably administered once a week (d1, d8, d15), and every 3 weeks is a treatment cycle, with a maximum of 6 treatment cycles.

In a preferred embodiment, the protein kinase inhibitor and chemotherapeutic drug are administered separately, simultaneously or sequentially.

In a preferred embodiment, after the cycle of combined treatment of the protein kinase inhibitor and the chemotherapeutic substance ends, the protein kinase inhibitor can be continued to be administered for treatment.

In a fourth aspect, the present disclosure provides a kit comprising an effective amount of the above-mentioned pharmaceutical composition.

In a preferred embodiment, in the kit, the protein kinase inhibitor, the topoisomerase II inhibitor or paclitaxel and derivatives thereof are respectively unit preparations with the same or different specifications. The protein kinase inhibitor is preferably an oral preparation, the topoisomerase II inhibitor is preferably an oral preparation, and the paclitaxel and derivatives thereof are preferably an intravenous drip preparation.

In a preferred embodiment, the protein kinase inhibitor and chemotherapeutic drug are respectively provided in separate containers, and the protein kinase inhibitor and chemotherapeutic drug may be administered simultaneously, successively or sequentially.

In a preferred embodiment, in the same package, the kit comprises:

a first container containing a protein kinase inhibitor; and a second container containing a chemotherapy drug.

Finally, the present disclosure also provides use of the compound of formula (II) in the preparation of a medicament for the treatment of platinum-refractory/platinum-resistant relapsed advanced ovarian cancer.

(II)

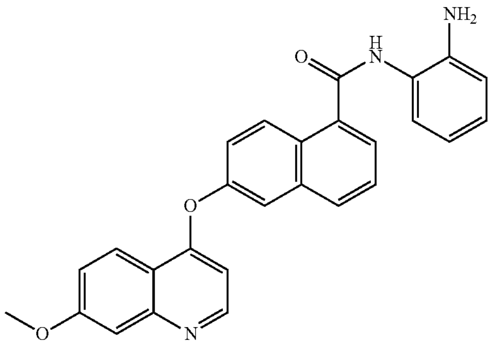

In the present disclosure, through the "single-arm, multi-center, non-randomized, open-label clinical trial to explore the efficacy and safety of chiauranib capsules for the treatment of relapsed and refractory advanced ovarian cancer", it is confirmed that in subjects with platinum-refractory/resistant relapsed advanced ovarian cancer who have received multiple chemotherapy, chiauranib single-agent has shown preliminary efficacy in tumor response. Through the "phase II multi-center clinical trial of chiauranib combined with chemotherapy in the treatment of platinum-refractory/platinum-resistant relapsed ovarian cancer", it is preliminarily suggested that the objective response rates of etoposide and paclitaxel in combination with chiauranib respectively in the treatment of platinum-refractory/resistant relapsed advanced ovarian cancer have been both improved. The response rate of etoposide alone is about 27%, the response rate of paclitaxel alone is about 21%, and the objective response rates of the two chemotherapy drugs in combination with chiauranib respectively are respectively 40% and 50%, indicating that the combination of chiauranib with etoposide or paclitaxel has achieved an unexpected synergistic effect in the treatment of platinum-refractory/resistant relapsed advanced ovarian cancer. According to the actual situation of the enrolled cases, it shows that the combination of chiauranib with etoposide or paclitaxel has an excellent effect in the treatment of platinum-refractory/resistant relapsed advanced (stage III and IV) malignant epithelial ovarian cancer, especially the malignant epithelial ovarian cancer at stage III and stage IV with metastasis.

As used herein, the terms “containing”, “comprising” or “including” mean the inclusion of the described elements, integers or steps, but not the exclusion of any other elements, integers or steps. Herein, when the terms “containing”, “comprising” or “including” are used, unless otherwise indicated, situations consisting of the described elements, integers or steps are also encompassed.

The term “prevention” comprises the inhibition or delay of the onset or frequency of a disease or disorder or symptoms thereof, and generally refers to the administration of a drug prior to the onset of disease signs or symptoms, particularly in at-risk individuals.

The term “treatment” as used herein refers to the slowing, arrest or reversal of the progression of cancer in a subject as evidenced by the alleviation or elimination of clinical or diagnostic symptoms of the disease. Treatment can comprise, for example, reduction in symptom severity, number of symptoms, or frequency of recurrence, such as inhibition on tumor growth, arrest of tumor growth, or regression of an existing tumor.

The term “pharmaceutical composition” refers to a non-fixed combination product or a fixed combination product. The term “non-fixed combination” means that the active ingredients, such as a protein kinase inhibitor and a chemotherapeutic drug, are administered to a patient as separate entities simultaneously, without a specific time limit, or at the same or different time intervals, or sequentially, wherein such administration provides prophylactically or therapeutically effective levels of the two active agents in the patient. In some embodiments, the two molecules, a protein kinase inhibitor and a chemotherapeutic drug, used in the pharmaceutical composition are administered at levels no greater than that when they are used alone. The term “fixed combination” means that the two active agents are administered to a patient simultaneously in the form of a single entity. The dosages and/or time intervals of the two active agents are preferably selected so that the combined use of each part produces a greater effect than that either component alone can achieve in the treatment of a disease or disorder. Each component may present in separate preparation respectively, the preparation form of which may be the same or different.

When referring to combination therapy, the term “therapeutically effective amount” as used herein refers to a dosage of combined administration to elicit the biological or medical response in the combined administration, as inhibiting or ameliorating clinical or diagnostic symptoms of one or more cancers comprising relapsed and refractory ovarian cancer. For example, when referring to combination therapy, the term “therapeutically effective amount” as used herein is the amount that results in a therapeutically effective and/or synergistic combined effect when administering together (sequentially or simultaneously) on the same or different days of the treatment cycle.

The term “administration” refers to the physical introduction of each active ingredient in the pharmaceutical composition of the present disclosure into an individual using any of a variety of methods and delivery systems known to those skilled in the art. Routes of administration for each active ingredient in the pharmaceutical composition of the present disclosure comprise oral, intravenous (such as infusion, also known as drip, or injection), intramuscular, subcutaneous, intraperitoneal, spinal, topical administration or other parenteral administration routes. The phrase “parenteral administration” as used herein refers to modes of administration other than enteral and topical administration, usually intravenously, and includes, intramuscular, intraarterial, intrathecal, intralymphatic, intralesional, intracapsular, intraorbital, intracardiac, intradermal, intraperitoneal, transtracheal, subcutaneous, subepidermal, intraarticular, subcapsular, subarachnoid, intraspinal, epidural and intrasternal injection or infusion, and in vivo electroporation. Correspondingly, each active ingredient in the pharmaceutical composition of the present disclosure can be formulated into capsules, tablets, injections (comprising infusions or injections), syrups, sprays, lozenges, liposomes or suppositories and the like.

The term “dosage” is the amount of drug that elicits a therapeutic effect. Unless otherwise stated, dosage is related to the amount of drug in free form. If the drug is in the form of a pharmaceutically acceptable salt, the amount of drug is increased proportionally to the amount of drug in free form. For example, the dosage will be stated on the product packaging or product information sheet.

The term “pharmaceutically acceptable” refers to those compounds, materials, compositions and/or dosage forms that are suitable for use in contact with human and animal tissues without undue toxicity, irritation, allergic reactions or other problems or complications, and are commensurate with a reasonable benefit/risk ratio.

DETAILED DESCRIPTION

The present disclosure discloses a pharmaceutical composition comprising a protein kinase inhibitor and a chemotherapeutic drug and use thereof, and those skilled in the art can learn from the content of this document and make appropriate improvements. It should be particularly noted that all similar substitutions and modifications are obvious to those skilled in the art, which are deemed to be included in the present disclosure. The application of the present disclosure has been described through the preferred embodiments, and it is obvious that relevant persons can make modifications or appropriate changes and combinations to the applications described herein without departing from the content, thought and scope of the present disclosure to implement and apply the technology of the present disclosure.

The present disclosure is further illustrated below by non-limiting examples, which is not intended to limit the scope encompassed by the present disclosure.

Unless otherwise defined, all technical and scientific terms used herein have the same meanings as commonly understood by those of ordinary skill in the art. For the purpose of the present disclosure, the following terms are defined below.

The term “about” when used in conjunction with a numerical value is meant to encompass the numerical value within a range having a lower limit that is 5% less than the specified numerical value and an upper limit that is 5% greater than the specified numerical value.

The term “adverse event” (AE) refers to an adverse medical event that occurs after a patient or clinical trial subject receives a drug/substance, but it is not necessarily causally related to the treatment. The relapse of pre-existing other disease that occurs during the course of the clinical study is included, whether or not its occurrence is related to the treatment. Invasive clinical examinations per se are not considered as adverse events, but the reasons for these examinations should be considered as adverse events.

Example 1 A Single-Arm, Multi-Center, Non-Randomized, Open-Label Clinical Trial to Explore the Efficacy and Safety of Chiauranib Capsules for the Treatment of Relapsed and Refractory Ovarian Cancer 1. Trial Design A single-arm, multi-center, non-randomized, open-label phase Ib trial.

Main inclusion criteria: Patients with histologically diagnosed epithelial ovarian cancer, fallopian tube cancer or primary peritoneal carcinoma; patients who had received platinum-based chemotherapy regimens, and platinum-resistant patients who achieved progressive or relapsed disease after had received ≥2 different chemotherapy regimens; platinum-sensitive patients who achieved progressive or relapsed disease after had received ≥2 different chemotherapy regimens, or who refused to receive further chemotherapy.

Medication regimen: 50 mg of chiauranib was taken orally every morning on an empty stomach, once a day, every 28 days as a treatment cycle, and there was no drug withdrawal interval between the treatment cycles. The treatment was continued until any of the following conditions occurred (whichever occurred first): progressive disease, intolerable toxicity reaction, death, withdrawal of informed consent, or loss to follow-up.

Efficacy indicators: The efficacy indicators were evaluated by investigators and imaging experts according to RECIST1.1 criteria.

Main: Objective response rate (ORR).

Secondary: Progression-free survival (PFS), time to progression (TTP), 16-week disease control rate (16W-DCR), duration of response (DOR) of disease, overall survival (OS).

2. Subject Population

Twenty-five patients with relapsed and refractory ovarian cancer were enrolled in the study, and the number of previous treatment regimens they had received was ≥3. 3 cases (12.0%) were sensitive to the last platinum-containing chemotherapy, and 22 cases (88.0%) were refractory or resistant to the last platinum-containing chemotherapy. As of the cut-off date for trial data (Mar. 20, 2019), 16 patients (64.0%) discontinued the treatment due to progressive disease, 3 patients (12.0%) discontinued the treatment due to adverse events, and other reasons for the discontinuation of the treatment comprised voluntary withdrawal of subjects, end of trial and loss to follow-up.

The full analysis set (FAS) and safety data set (SS) were used for analysis, and 25 subjects were included in each data set.

3. Efficacy Results

The evaluation of various efficacy indicators is shown in Table 1. Among the 25 subjects, the confirmed best efficacy was partial response (PR) in 1 case (4.0%), stable disease (SD) in 14 cases (56.0%), progressive disease (PD) in 7 cases (28.0%), and not evaluable (NE) in 3 cases (12.0%). ORR was 4.0%.

As of the cut-off date for trial data (Mar. 20, 2019), 12 study events (progressive disease or death) had achieved PFS, with a median PFS of 3.7 (95% CI, 1.8~NE) months. The median TTP was 3.7 (95% CI, 1.8~NE) months, the 16W-DCR was 32.0%, and the median DOR and OS could not be estimated so far.

TABLE 1

Efficacy results of chiauranib capsule in the treatment of relapsed and refractory ovarian cancer

| | N = 25 |
|---|---|
| Best efficacy assessment, n(%) | |
| CR | 0 |
| PR | 1 (4.0) |
| SD | 14 (56.0) |
| PD | 7 (28.0) |
| NE | 3 (12.0) |
| Objective response rate, % (95% CI) | 4.0 (0.10%, 20.35%) |
| 16-week disease control rate, % (95% CI) | 32.0 (15.0%, 53.5%) |
| Progression-free survival, median(95% CI), month | 3.7 (1.8, NE) |
| Event | 12 |
| Censoring | 13 |
| Time to progression, median(95% CI), month | 3.7 (1.8, NE) |
| Event | 11 |
| Censoring | 14 |
| Duration of response, median(95% CI), month | NE (NE, NE) |
| Event | 0 |
| Censoring | 2 |
| Overall survival, median(95% CI), month | NE (6.0, NE) |
| Event | 11 |
| Censoring | 14 |

4. Efficacy Conclusion

In subjects with platinum-refractory/resistant relapsed ovarian cancer who had received multiple chemotherapies, chiauranib single-agent showed primary efficacy of tumor response.

5. Safety Evaluation

The safety indicators comprised adverse events, vital signs, ECG and abnormal laboratory results, which were evaluated according to CTCAE V4.03. Twenty-five patients with relapsed and refractory ovarian cancer were enrolled in the study and included in the safety data set (SS) for analysis. The results are shown in Table 2.

TABLE 2

Safety evaluation results of chiauranib capsule in the treatment of relapsed and refractory ovarian cancer

| By severity | By frequency of occurrence |
|---|---|
| Adverse event leading to death | Common adverse event |
| One patient (4.0%) died due to the "multiple organ dysfunction syndrome". Cause of death: the patient with advanced ovarian cancer had multiple relapses in the postoperative chemotherapy and was insensitive to chemotherapy with change of chemotherapy regimens; the patient was admitted to hospital for loss of consciousness with no obvious | All 25 (100%) subjects experienced at least one common adverse event. The adverse events with relatively high incidence were: diarrhea in 18 cases (72.0%), loss of appetite in 16 cases (64.0%), fatigue in 16 cases (64.0%), proteinuria in 15 cases (60.0%), weight loss in 14 cases (56.0%), abdominal pain in 13 cases (52.0%), |

TABLE 2-continued

| Safety evaluation results of chiauranib capsule in the treatment of relapsed and refractory ovarian cancer | |
|---|---|
| By severity | By frequency of occurrence |
| incentive, and still presented multiple organ failure after active treatment. This event was judged to be undetermined with chiauranib. | hypertension in 11 cases (44.0%), etc. |
| Serious adverse event | |
| 9 cases of serious adverse events occurred in 8 patients (32.0%), and 5 cases were judged to be related to chiauranib (definitely related, possibly related, undetermined), which were respectively 1 case of liver function damage, 1 case of bile duct obstruction, 1 case of electrolyte disturbance, 1 case of hypokalemia, and 1 case of death (multiple organ failure) mentioned above. Liver function damage is a known adverse event of chiauranib, and chiauranib has caused the adverse event of hyponatremia in the past. | |
| Adverse event leading to the discontinuation of the treatment | |
| 3 patients (12.0%) discontinued chiauranib therapy due to adverse events, which were respectively 1 case of multiple organ dysfunction syndrome, 1 case of bile duct obstruction, and 1 case of electrolyte disturbance. | |
| Adverse event leading to the reduction of the dosage of chiauranib | |
| One patient (4.0%) had a dosage reduction of chiauranib due to an adverse event, which was an increase in serum creatine phosphokinase MB. | |
| Adverse event leading to the suspension of chiauranib | |
| 11 patients (40.7%) suspended chiauranib due to adverse events, which were 2 cases of decreased platelet count, 3 cases of hypertension, 2 cases of proteinuria, 1 case of increased alanine aminotransferase, 1 case of increased aspartate aminotransferase, 1 case of ventricular dysfunction, 1 case of infection, 1 case of decreased appetite and 1 case of palmoplantar erythema syndrome. | |

The current data suggest that the toxicity characteristics of chiauranib single-agent therapy are similar to those reported in VEGFR target drugs (eg: sorafenib, sunitinib, etc.), which can be tolerated by most subjects, and are safe controllably.

Example 2 A Phase II Multi-Center Clinical Trial of Chiauranib in Combination with Chemotherapy in the Treatment of Platinum-Refractory/Platinum-Resistant Relapsed Advanced Ovarian Cancer

1. Trial Design

A multi-center, randomized, and open-label phase II trial.

The subjects were stratified according to whether or not the treatment-free interval (TFI) was more than or equal to 3 months at the time of screening, and the stratified subjects were randomly assigned to chiauranib in combination with etoposide group (CE group) or chiauranib in combination with paclitaxel group (CP group) according to a ratio of 1:1.

The trial was divided into two phases: pre-trial and formal trial. Before the start of the formal trial, 3 subjects were enrolled into each group for the pre-trial to preliminarily evaluate the safety of chiauranib in combination with chemotherapeutic drugs, and analyze the potential effects of chemotherapy drugs on the pharmacokinetics of chiauranib. After the first cycle of safety and pharmacokinetic evaluation was completed in all pre-trial subjects, the enrollment of the formal trial began.

Main inclusion criteria: Patients with histologically or cytologically diagnosed epithelial ovarian cancer, fallopian tube cancer or primary peritoneal carcinoma; patients with platinum-refractory or platinum-resistant relapsed ovarian cancer; patients who had previously received ≥1 line of platinum-containing chemotherapy (platinum-containing treatment for at least 4 treatment cycles), and patients with platinum-refractory or platinum-resistant cancer who had received ≤2 lines of therapy.

Medication regimen: The medication regimen comprised two treatment stages, a stage of chiauranib in combination with chemotherapy and a stage of maintenance by chiauranib single-agent. All subjects were treated until progressive disease, intolerable toxicity, withdrawal of informed consent or death occurred (whichever occurred first).

Stage of chiauranib in combination with chemotherapy: CE group: Chiauranib capsule: In the pre-trial phase, it was orally administered at 25 mg, once a day. After the sampling of the pharmacokinetics study at the time point specified in the protocol was completed, the investigator decided whether or not to increase the administration to 50 mg orally, once a day by observing the tolerance and preliminary efficacy comprehensively; in the formal trial phase, it was orally administered at 50 mg on an empty stomach every morning, once a day, and administered continuously. Etoposide soft capsule: It was orally administered at 50 mg every morning on an empty stomach, continuously administered for 21 days and withdrawn for 7 days. Every 28 days was a treatment cycle, with a maximum of 6 treatment cycles. CP group: The administration regimens of chiauranib in the pre-trial and formal trial phases were the same as that in the CE group. Paclitaxel injection: It was administered at 60 $mg/m^2$ via intravenous infusion, once a week (d1, d8, d15), and every 3 weeks was a treatment cycle, with a maximum of 6 treatment cycles.

Stage of maintenance by chiauranib single-agent: CE group and CP group both received maintenance therapy of chiauranib single-agent.

Efficacy indicators: The efficacy evaluation was performed using the RECIST version 1.1 (2009) criteria for solid tumors.

Main: Progression free survival (PFS).

Secondary: Objective response rate (ORR), overall survival (OS), time to progression (TTP), duration of response (DOR) of disease.

2. Subject Population

As of Dec. 26, 2019, a total of 21 patients (10 in CE group and 11 in CP group) were enrolled. The duration of treatment for the enrolled subjects was between 0-5 cycles, and the following efficacy results were based on the evaluable data before the cut-off date.

3. Efficacy Results

The evaluation of various efficacy indicators is shown in Table 3. 11 of the 21 subjects had efficacy evaluation record (5 in the CE group and 6 in the CP group). The best efficacy response showed that in the CE group, 2 cases (40.0%) achieved PR, and 3 cases achieved SD; in the CP group, 3 cases (50.0%) achieved PR, 2 cases achieved SD, and 1 case achieved PD.

TABLE 3

Efficacy results of chiauranib capsule in combination with chemotherapy in the treatment of relapsed and refractory advanced ovarian cancer

| Best efficacy response | CE (N = 10) | CP (N = 11) |
|---|---|---|
| No efficacy evaluation | 5 | 5 |
| Efficacy evaluation | 5 | 6 |
| CR (complete response) | 0 | 0 |
| PR (partial response) | 2 (40.0) | 3 (50.0) |
| SD (stable disease) | 3 (60.0) | 2 (33.3) |
| PD (progressive disease) | 0 | 1 (16.7) |

4. Efficacy Conclusion

Historical data show that in the treatment of platinum-refractory/resistant relapsed advanced ovarian cancer, the response rate of etoposide single-agent is about 27%, and the response rate of paclitaxel single-agent is about 21%. The current data suggest that the response rates of etoposide and paclitaxel in combination with chiauranib respectively are respectively 40% and 50%, indicating that the combination of chiauranib with etoposide or paclitaxel has achieved an unexpected synergistic effect in the treatment of platinum-refractory/resistant relapsed advanced ovarian cancer. According to the actual situation of the enrolled cases, it shows that the combination of chiauranib with etoposide or paclitaxel has an excellent effect in the treatment of platinum-refractory/resistant relapsed advanced (stage III and IV) malignant epithelial ovarian cancer, especially the malignant epithelial ovarian cancer at stage III and stage IV with metastasis.

5. Safety Evaluation

The safety indicators comprised various vital signs, adverse events and laboratory inspection indicators, which were detected or observed for safety evaluation. The severity of adverse events was judged according to CTCAE V4.03 criteria.

As of Dec. 26, 2019, a total of 21 patients (10 in CE group and 11 in CP group) were enrolled. The duration of treatment for the enrolled subjects was between 0-5 cycles, and the safety results were based on the evaluable data before the cut-off date. The results are shown in Table 4.

TABLE 4

Safety evaluation results of chiauranib capsule in combination with chemotherapy in the treatment of relapsed and refractory advanced ovarian cancer
Safety results

| By severity | By frequency of occurrence |
|---|---|
| Adverse event leading to death | Common adverse event |
| None. | CE group: All 10 (100%) subjects had at least one adverse event. The adverse events with relatively high incidence were: nausea in 7 cases (70.0%), decreased white blood cell count in 7 cases (70.0%), decreased neutrophil count in 6 cases (60.0%), decreased appetite in 6 cases (60.0%), fatigue in 5 cases (50.0%), vomiting in 5 cases (50.0%) and so on. |
| Serious adverse event | |
| One serious adverse event occurred, which was grade III gastrointestinal dysfunction (nausea, vomiting), which was judged to be possibly related to chiauranib and possibly related to paclitaxel. Nausea and vomiting are known adverse events of chiauranib. | |
| Adverse event of special concern | |
| None. | CP group: 8 out of 11 subjects (72.7%) had at least one adverse event. The adverse events with relatively high incidence were: decreased neutrophil count in 6 cases (54.5%), decreased white blood cell count in 6 cases (54.5%), anemia in 4 cases (36.4%), hypertension in 4 cases (36.4%) and so on. |

The current data suggest that the types of adverse events of etoposide and paclitaxel in combination with chiauranib respectively are similar to those reported in each chemotherapeutic drug single-agent and chiauranib single-agent, and no new safety signals have been found. The incidence of adverse events has increased, but most patients can tolerate it, no treatment has been terminated due to adverse events, and the safety is controllable.

The present disclosure has been introduced in detail above, and the principles and implementations of the present disclosure are described herein by using specific examples. The descriptions of the above examples are only used to help understand the method and core idea of the present disclosure, including the best mode. It also enables any person skilled in the art to practice the present disclosure, including making and using any devices or systems, and implementing any combined methods. It should be noted that for those skilled in the art, several improvements and modifications can also be made to the present disclosure without departing from the principle of the present disclosure, and these improvements and modifications also fall within the protection scope of the claims of the present disclosure. The scope of patent protection of the present disclosure is defined by the claims, and may include other examples that occur to those skilled in the art. If such other examples have structural elements that do not differ from the literal language of the claims, or if they include equivalent structural elements with insubstantial differences from the literal expressions of the claims, they are also intended to be within the scope of the claims.

The invention claimed is:

1. A method for treating platinum-refractory/platinum-resistant relapsed ovarian cancer, comprising administering a therapeutically effective amount of a pharmaceutical composition to a patient in need, wherein the pharmaceutical composition comprises a protein kinase inhibitor and a chemotherapeutic drug, wherein the protein kinase inhibitor is a compound of formula (II):

(II)

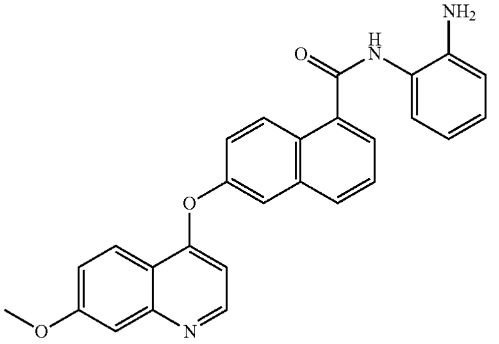

in free form, salt form, enantiomer or diastereomer thereof, wherein the chemotherapeutic drug is etoposide or paclitaxel.

2. The method according to claim 1, wherein the cancer is platinum-refractory/platinum-resistant relapsed advanced ovarian cancer.

3. The method according to claim 1, wherein the protein kinase inhibitor is used at an amount within the range of 1-100 mg, etoposide is used at an amount within the range of 1-100 mg, and paclitaxel is used at an amount within the range of 10-200 $mg/m^2$.

4. A method for treating platinum-refractory/platinum-resistant relapsed ovarian cancer, comprising administering a therapeutically effective amount of a pharmaceutical composition to a patient in need, wherein the pharmaceutical composition comprises a compound of formula (II)

(II)

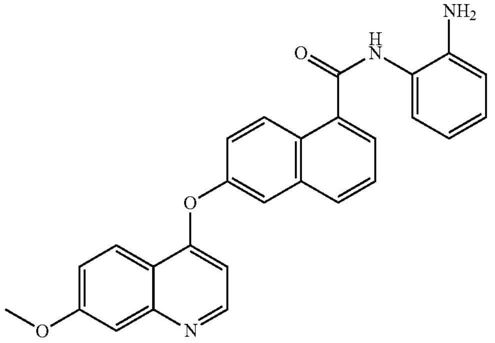

in combination with etoposide or paclitaxel.

5. The method according to claim 4, wherein the platinum-refractory/platinum-resistant relapsed ovarian cancer is platinum-refractory/platinum-resistant relapsed advanced ovarian cancer.

6. The method according to claim 4, wherein the compound of formula (II) is used at an amount within the range of 1-100 mg, etoposide is used at an amount within the range of 1-100 mg, and paclitaxel used at an amount within the range of 10-200 $mg/m^2$.

* * * * *